US008768031B2

(12) United States Patent
Mistretta et al.

(10) Patent No.: US 8,768,031 B2
(45) Date of Patent: Jul. 1, 2014

(54) TIME RESOLVED DIGITAL SUBTRACTION ANGIOGRAPHY PERFUSION MEASUREMENT METHOD, APPARATUS AND SYSTEM

(75) Inventors: Charles A. Mistretta, Madison, WI (US); Charles M. Strother, Madison, WI (US)

(73) Assignees: Mistretta Medical, LLC, Madison, WI (US); CMS Medical, LLC, Madison, WI (US)

( * ) Notice: Subject to any disclaimer, the term of this patent is extended or adjusted under 35 U.S.C. 154(b) by 433 days.

(21) Appl. No.: 13/250,376

(22) Filed: Sep. 30, 2011

(65) Prior Publication Data
US 2012/0114217 A1    May 10, 2012

Related U.S. Application Data

(60) Provisional application No. 61/389,086, filed on Oct. 1, 2010.

(51) Int. Cl.
| G06T 7/00 | (2006.01) |
| A61B 5/00 | (2006.01) |
| G01R 33/563 | (2006.01) |
| A61B 6/00 | (2006.01) |
| G06T 11/00 | (2006.01) |

(52) U.S. Cl.
CPC .............. *A61B 6/4441* (2013.01); *A61B 6/507* (2013.01); *A61B 6/504* (2013.01); *G06T 2211/404* (2013.01); *A61B 6/481* (2013.01); *G06T 11/006* (2013.01)

USPC ........... 382/131; 382/128; 382/130; 382/132; 600/363; 600/419

(58) Field of Classification Search
USPC ........... 382/131, 128, 130, 132; 600/363, 419
See application file for complete search history.

(56) References Cited

U.S. PATENT DOCUMENTS

| 4,482,918 | A | 11/1984 | Keyes et al. |
| 6,317,621 | B1 | 11/2001 | Graumann et al. |
| 6,823,204 | B2 | 11/2004 | Grass et al. |
| 6,983,182 | B2 | 1/2006 | Mistretta |
| 7,020,314 | B1 | 3/2006 | Suri et al. |
| 7,054,405 | B2 * | 5/2006 | Edic et al. .......................... 378/4 |
| 7,305,062 | B2 | 12/2007 | Hambuchen et al. |
| 7,545,901 | B2 | 6/2009 | Mistretta |
| 7,590,442 | B2 | 9/2009 | Boese et al. |
| 7,738,626 | B2 | 6/2010 | Weese et al. |

(Continued)

FOREIGN PATENT DOCUMENTS

WO    WO-2006/106470    10/2006

OTHER PUBLICATIONS

Dumay, et al. "Developments towards slice-wise three-dimensional reconstruction of the distribution of the contrast perfusion in the myocardial muscle from biplane angiographic views." International Journal of Cardiac Imaging. 5. (1990): 213-224. Print.*

(Continued)

*Primary Examiner* — Michael A Newman
(74) *Attorney, Agent, or Firm* — Foley & Lardner LLP

(57) ABSTRACT

A method is disclosed of providing time dependent three dimensional imaging of a region of a patient comprising blood vessels in a perfusion bed.

23 Claims, 17 Drawing Sheets

(56) References Cited

U.S. PATENT DOCUMENTS

| | | | |
|---|---|---|---|
| 8,009,885 B2 | 8/2011 | Grass et al. | |
| 8,285,360 B2 * | 10/2012 | Kabasawa | 600/419 |
| 2001/0007593 A1 | 7/2001 | Oosawa | |
| 2004/0116812 A1 | 6/2004 | Selzer et al. | |
| 2005/0080328 A1 | 4/2005 | Vass et al. | |
| 2005/0084060 A1 | 4/2005 | Seppi et al. | |
| 2005/0232389 A1 | 10/2005 | Klingenbeck-Regn | |
| 2006/0165213 A1 | 7/2006 | Hambuchen et al. | |
| 2006/0173297 A1 | 8/2006 | Popescu | |
| 2006/0250386 A1 | 11/2006 | Movassaghi et al. | |
| 2007/0009080 A1 | 1/2007 | Mistretta | |
| 2007/0055148 A1 | 3/2007 | Klingenbeck-Regn | |
| 2007/0183569 A1 | 8/2007 | Boese et al. | |
| 2008/0051648 A1 | 2/2008 | Suri et al. | |
| 2008/0192997 A1 | 8/2008 | Grass et al. | |
| 2008/0212857 A1 | 9/2008 | Pfister et al. | |
| 2008/0243435 A1 | 10/2008 | Deinzer et al. | |
| 2008/0300478 A1 | 12/2008 | Zuhars et al. | |
| 2008/0304728 A1 | 12/2008 | Licato et al. | |
| 2009/0010380 A1 | 1/2009 | Gotoh | |
| 2009/0074277 A1 | 3/2009 | Deinzer et al. | |
| 2009/0088830 A1 | 4/2009 | Mohamed et al. | |
| 2009/0093712 A1 | 4/2009 | Busch et al. | |
| 2010/0053209 A1 | 3/2010 | Rauch et al. | |
| 2010/0061611 A1 | 3/2010 | Xu et al. | |
| 2010/0201786 A1 | 8/2010 | Schaefer et al. | |
| 2010/0296623 A1 | 11/2010 | Mielekamp et al. | |
| 2011/0037761 A1 | 2/2011 | Mistretta et al. | |
| 2011/0038517 A1 | 2/2011 | Mistretta et al. | |
| 2013/0039559 A1 * | 2/2013 | Grass et al. | 382/131 |
| 2013/0123611 A1 * | 5/2013 | Riederer et al. | 600/419 |

OTHER PUBLICATIONS

International Search Report and Written Opinion for PCT Application No. PCT/US2012/042491, mailed Mar. 4, 2013, 10 pages.

Chen et al., "Blood Flow Measurement by Cone-Beam CT Bolus Imaging", Proceedings of the SPIE, vol. 6143, 61432J, 2006, 12 pages.

International Search Report and Written Opinion for PCT Application No. PCT/US2010/045637, mail date Apr. 12, 2011, 7 pages.

International Search Report and Written Opinion for PCT Application No. PCT/US2011/022120, mail date Aug. 26, 2011, 9 pages.

Kohler et al., "Method for Flow Reconstruction from Dynamic X-Ray Projection Measurements", Nuclear Science Symposium Conference Record, 2004 IEEE, vol. 5, Oct. 2004, 4 pages.

Lessard et al., "Automatically Driven Vector for Line Segmentation in 2D and Biplane Imaging Modality", 15 International Conference of Image Analysis and Processing, Italy, Sep. 8-11, 2009, 9 pages.

Liu et al., "Renal Perfusion and Hemodynamics: Accurate in Vivo Determination at CT with a 10-Fold Decrease in Radiation Dose and HYPR Noise Reduction", Radiology, vol. 253, No. 1, Oct. 2009, 8 pages.

Mistretta et al., "HYPR: Constrained Reconstruction for Enhanced SNR in Dynamic Medical Imaging", Medical Imaging 2008: Physics of Medical Imaging, Proceedings of the SPIE, vol. 6913, 2008, 9 pages.

Nth Root, http://www.mathisfun.com/numbers/nth-root.html, Archived on Dec. 21, 2007, Retrieved Jul. 10, 2012 from http://web.archive.org/web/20071221121146/http://www.mathisfun.com/numbers/nth-root.html, 6 pages.

Pollmann et al., "Four Dimensional Intravenous Cone-Beam Computed Tomographic Subtraction Angiography", Investigative Radiology, vol. 43, No. 11, Nov. 2008, 9 pages.

Schmitt et al., "An X-Ray-Based Method for the Determination of the Contrast Agent Propagation in 3-D Vessel Structures", IEEE Transactions on Medical Imaging, vol. 21, No. 3, Mar. 2002, 12 pages.

Schmitt et al., "Reconstruction of Blood Propagation in Three-Dimensional Rotational X-ray Angiography (3D-RA)", Computerized Medical Imaging and Graphics, vol. 29, Issue 7, Oct. 2005, 14 pages.

Waechter et al., "Using Flow Information to Support 3D Vessel Reconstruction from Rotational Angiography", Med. Phys. 35 (7), Jul. 2008, 15 pages.

* cited by examiner

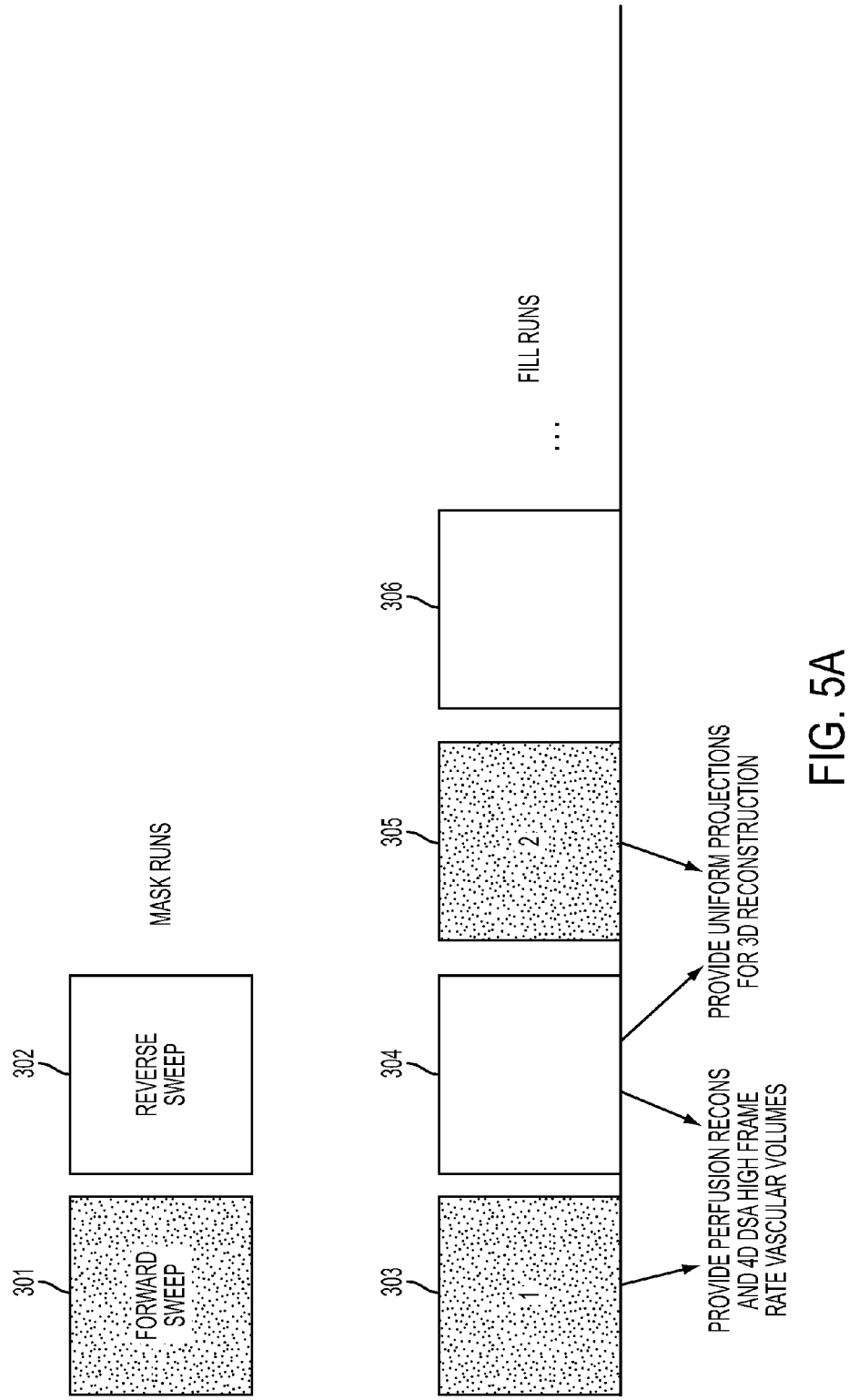

TIME RESOLVED DIGITAL SUBTRACTION ANGIOGRAPHY PERFUSION MEASUREMENT METHOD, APPARATUS AND SYSTEM

CROSS REFERENCE TO RELATED APPLICATIONS

This application claims the benefit under 35 U.S.C. §119(e) of U.S. Provisional Application Ser. No. 61/389,086, filed Oct. 1, 2010, the entire contents of which are incorporated herein by reference.

BACKGROUND

Estimates of tissue perfusion parameters are important for diagnosis, treatment planning and treatment of a variety of diseases e.g. ischemic conditions and tumors involving the brain, heart, liver as well as other organs. Perfusion measurements performed with conventional digital subtraction angiography (DSA) are very limited since the two-dimensional nature of these examinations superimposes the tissue perfusion bed from multiple overlapping planes. For example, attempts to measure coronary artery flow reserve using a 2D technique may be limited by the overlapping of vascular beds in the available projection images.

With time resolved 3D information (referred to herein as "4D"), the perfusion signals from the tissue can be separately displayed for any plane without overlap. U.S. patent application Ser. No. 12/692,340, filed Jan. 22, 2010 and entitled SYSTEM AND METHOD FOR FOUR DIMENSIONAL ANGIOGRAPHY AND FLUOROSCOPY describes 4D DSA techniques for displaying time resolved 3D image volumes. The entire contents of the foregoing application are incorporated by reference herein. This method is based on angiographic acquisitions obtained using a C-arm flat detector angiographic apparatus. In this implementation a limited number (e.g., two or less) projections are used in conjunction with a 3D rotational DSA reconstruction to generate a time resolved sequence of 3D vascular volumes. However, signals in the perfusion bed were not adequately reconstructed. As used herein, the term 4D DSA vascular reconstruction refers to a measurement of this type.

Accordingly, it would be advantageous to provide an imaging method which provides time resolved 3D volume reconstructions which preserve information about the perfusion bed.

SUMMARY

The inventors have realized that for preservation of the signals in the tissue perfusion bed it is necessary to use a larger number of projections. However, in order to maintain adequate temporal resolution, the number of projections used must be less than the usual number that are used for reconstructing a time independent the 3D vascular volumes. In the case of the CT-like images acquired with a flat detector C-arm angiographic system (as described in detail below), limiting the number of projections can be accomplished by using angular sectors of projections the total temporal duration of which is limited to a clinically acceptable value, typically a fraction of a second (e.g., 1.0 seconds or less, 0.5 seconds or less, 0.25 seconds or less, etc.). For the purpose of generating artifact free, high detail images the use of angular sectors significantly smaller than 180 degrees leads to image artifacts. Accordingly, the techniques describe herein combine reconstruction (e.g., by filtered back projection) of these limited sectors with reconstruction constraints (e.g. based on a time independent 3D volume created using projection spanning angles of about 180 degrees or more) to reduce the impact of these artifacts on image quality.

In typical C-arm applications described herein the low spatial frequency information comes from limited sector reconstructions and high spatial frequency information is provided by an acquisition comprised of projections from a complete rotation. This exploits the fact that the perfusion signal typically is primarily of low spatial frequency. This fact can be exploited to improve the quality of narrow sector reconstructions by diminishing the role of high spatial frequency artifacts as described below.

The extension of the 4D DSA technique to include not only vascular information but information describing the perfusion of the vascular bed provides a new dimension for C-arm systems in the facilitation of interventional techniques and their quantitative evaluation.

In some applications it is important to extract physiological parameters from 4D perfusion measurements. Parameters extracted may include tissue blood volume, maximum contrast achieved (Cmax), which is related to blood volume, time to peak opacification (TTP), mean transit time (MTT) and flow parameters such as Cmax/TTP. In conventional x-ray angiographic techniques, extraction of these parameters was corrupted by the need to integrate them across two dimensional projections, causing overlap of tissue and vascular beds. The present disclosure describes techniques which avoid such overlap and enable measurement of these perfusion parameters using x-ray angiographic techniques with the same accuracy and precision that is known to be possible using traditional CT and MRI methods.

In one aspect, a method of providing time dependent three dimensional imaging of a region of a patient including blood vessels in a perfusion bed, the method including: generating a time independent 3D volume reconstruction of the region based on a series of image projections of the region acquired over a wide range of projection angles; receiving a series of time resolved image projections of the region; and generating a time resolved series of limited sector 3D volume reconstructions of the region. Generating each limited sector 3D volume reconstruction in the series includes: selecting a respective limited sector set of image projections from the series of time resolved image projections, the limited sector set of image projections including (or, in some embodiments consisting of or consisting essentially of) projections in a limited range of projection angles less than the wide range of projection angles; and generating the limited sector 3D volume reconstruction based on the respective limited sector set of projections and constrained by the time independent 3D volume reconstruction.

In some embodiments, the projections are subtracted angiography projections.

In some embodiments, the wide range of angles corresponds to angles spaced over a range of about 180 degrees or more.

In some embodiments, the limited range of angles corresponds to angles spaced over a range of about 100 degrees or less.

In some embodiments, each limited sector set of image projections is selected based on a sliding window applied to the series of time resolved image projections of the region.

In some embodiments, generating each limited sector 3D volume reconstruction based on the respective limited sector set of image projections and constrained by the time independent 3D volume reconstruction includes: generating a limited sector 3D volume reconstruction having relatively low spatial frequency components derived primarily from the respective limited sector set of projections and high frequency components derived primarily from the time independent 3D volume reconstruction.

In some embodiments, generating each limited sector 3D volume reconstruction based on the respective limited sector set of image projections and constrained by the time independent 3D volume reconstruction includes: generating a limited sector 3D volume reconstruction based on the image projections; convolving the limited sector 3D volume reconstruction; and multiplying the convolved limited sector 3D volume reconstruction with the time independent 3D volume reconstruction to generate a respective limited sector 3D volume reconstruction constrained by the time independent 3D volume reconstruction.

In some embodiments, generating each limited sector 3D volume reconstruction based on the respective limited sector set of image projections and constrained by the time independent 3D volume reconstruction includes: convolving the image projections in the limited sector set of projections; generating a limited sector 3D volume reconstruction based on the convolved image projections; and multiplying the limited sector 3D volume with the time independent 3D volume reconstruction to generate a respective limited sector 3D volume reconstruction constrained by the time independent 3D volume reconstruction.

In some embodiments, during an imaging period: a contrast fluid flows into or out of the blood vessels in the region of the patient during a flow period; the contrast fluid flow reaches an equilibrium state in the blood vessels in the region during an equilibrium period. In some embodiments, the time independent 3D volume reconstruction is based on projections obtained during the equilibrium period; and the time resolved series of image projections is obtained during the flow period.

In some embodiments, during an imaging period: a contrast fluid flows into the blood vessels in the region of the patient during an inflow period; the contrast fluid flow reaches an equilibrium state in the blood vessels the region during an equilibrium period; the contrast fluid flows out of the blood vessels in the region during an inflow period. In some embodiments, the time independent 3D volume reconstruction is based on projections obtained during the equilibrium period; an inflow set of the time resolved series of image projections is obtained during the inflow period; and an outflow set of the time resolved series of image projections is obtained during the outflow period.

Some embodiments include, for at least one limited sector set of projections: a) generating a calculated 3D volume reconstruction based on the projections in the limited sector set of image projections; b) generating a set of calculated projections based on the calculated 3D volume reconstructions; c) comparing the set of calculated projections to the projections in the limited sector set of image projections; d) modifying the limited sector set of projections of the based on the comparison; e) generating a modified calculated 3D volume reconstruction based on the modified projections; f) generating a set of modified calculated projections based on the modified calculated 3D volume reconstruction; g) comparing the set of modified calculated projections to the modified projections used to generate the modified calculated 3D volume reconstruction; and h) further modifying the modified projections of the based on the comparison. Some embodiments include iteratively repeating steps e-h to improve the similarity of the modified calculated projections to the projections used to generate the limited sector 3D volume reconstruction. In some embodiments, at least one limited sector 3D volume reconstruction is based on the modified projections. In some embodiments, generating calculated projections based on the limited sector 3D volume reconstructions includes applying a Radon transformation to the limited sector 3D volume reconstructions. In some embodiments, at least one of the calculated 3D volume reconstruction and the modified calculated 3D volume reconstructions is constrained by the time independent 3D volume reconstruction. In some embodiments, the calculated 3D volume reconstruction and the modified calculated 3D volume reconstruction are not constrained by the time independent 3D volume reconstruction.

Some embodiments include, for at least one 3D volume reconstruction: a) generating a set of calculated projections based on the 3D volume reconstruction; b) generating a difference projection based on a difference between the set of calculated projections and the acquired projections on which the 3D volume reconstruction is based; c) generating a difference 3D volume reconstruction based on the difference projections; and d) creating a modified 3D volume by adding the difference 3D volume to the 3D volume reconstruction. Some embodiments include iteratively repeating steps a-d using the modified 3D volume as the starting 3D volume for each iteration. In some embodiments, generating calculated projections based on the 3D volume includes applying a Radon transformation to the limited sector 3D volume reconstructions.

Some embodiments include generating at least one parametric image based on the time dependent series of limited sector reconstructions.

In some embodiments, generating at least one limited sector 3D volume reconstruction based on the respective limited sector set of image projections includes: generating a low spatial frequency 3D volume reconstruction based on the low spatial frequency components of projections in a first subrange of the limited angular range; generating a high spatial frequency 3D volume reconstruction based on the high spatial frequency components of projection in a second subrange of the limited angular range smaller than the first; and generating the limited sector 3D volume reconstruction based on the low spatial frequency 3D volume reconstruction and the high spatial frequency 3D volume reconstruction. Some embodiments include: dividing the time independent 3D volume reconstruction into high and low spatial frequency components; generating calculated projections based on the divided high and low spatial frequency components; identifying calculated projections corresponding to the first and second subranges; reconstructing a calculated limited sector 3D volume reconstruction based on the calculated projections corresponding to the first and second angular subranges; and weighting the limited sector 3D volume reconstruction by multiplication with the time independent 3D volume formed using the full angular range and all frequencies.

In some embodiments, prior to generating the limited sector 3D volume reconstructions, the corresponding limited sector set of projections is renormalized to have equal integrals over all rays.

Some embodiments include: generating an initial series of time resolved 3D volume reconstructions each based on a limited number of projections constrained by the time independent 3D volume reconstruction; renormalizing the series of image projections of the region acquired over a wide range of projection angles of time independent projections based on the initial series; and generating an improved time independent 3D volume based on the renormalized series. In some embodiments, the limited number is two or less. In some embodiments, the initial series of time resolved 3D volume reconstructions are subtracted angiography volumes which do not accurately show the perfusion bed.

In some embodiments, the time dependent series of image projections includes a vessel suppressed projection.

In some embodiments, a blurring in the time resolved 3D volume reconstructions caused by the use of the limited sector sets of projections is comparable to blurring caused by the convolution.

In some embodiments, selecting a respective limited sector set of image projections from the series of time resolved image projections includes selecting a set of projections disposed substantially symmetrically about a plane of interest in the region.

Some embodiments include compensating for angular variations in the time resolved series of 3D volume reconstructions based on variations related to the anatomy in the region. In some embodiments, compensating for angular variations in the time resolved series of 3D volume reconstructions based on variations related to the anatomy in the region includes: observing a time dependence of a given region in the perfusion bed in the time resolved series of 3D volume reconstructions; observing a time dependence of a nearby blood vessel in the time resolved series of 3D volume reconstructions; measuring the time dependence of a corresponding blood vessel in a time resolved vascular reconstruction that is not subject the angular intensity variations; and correcting voxels corresponding to the perfusion bed in the time resolved series of 3D volume reconstructions based on the time dependence of the blood vessel in the time resolved series of 3D volume reconstructions and the time dependence of the corresponding blood vessel in a time resolved vascular reconstruction. In some embodiments, the blood vessel information includes reconstruction information which is not substantially subject to the angular variations.

In some embodiments, the time resolved series of image projections are obtained using a C-arm X-ray system. In some embodiments, the image projections are obtained during one or more sweeps of the C-arm. In some embodiments, each limited sector set of image projections corresponds to a time interval during the one or more sweeps. In some embodiments, the image projections are obtained during multiple sweeps of the C-arm, and using a single contrast injection.

In another aspect, a system is disclosed including: a C-arm X-ray system; a processor configured to receive projection information from the X-ray system and implement any of the methods described above based on the projection information.

In another aspect, an apparatus is disclosed including a processor configured to receive projection information from the X-ray system and implement any of the methods described above based on the projection information.

In another aspect computer program product is disclosed including a computer usable medium having a computer readable program code embodied therein, said computer readable program code adapted to be executed to implement any of the methods described above.

Various embodiments may include any of the above described elements, steps, techniques, etc, either alone or in any suitable combination.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

FIG. 5A illustrates a data acquisition strategy that permits acquisition of 4D DSA time frames, perfusion time frames and the constraining image from a single contrast injection and multiple C-arm rotations.

DETAILED DESCRIPTION

Figure 1A:
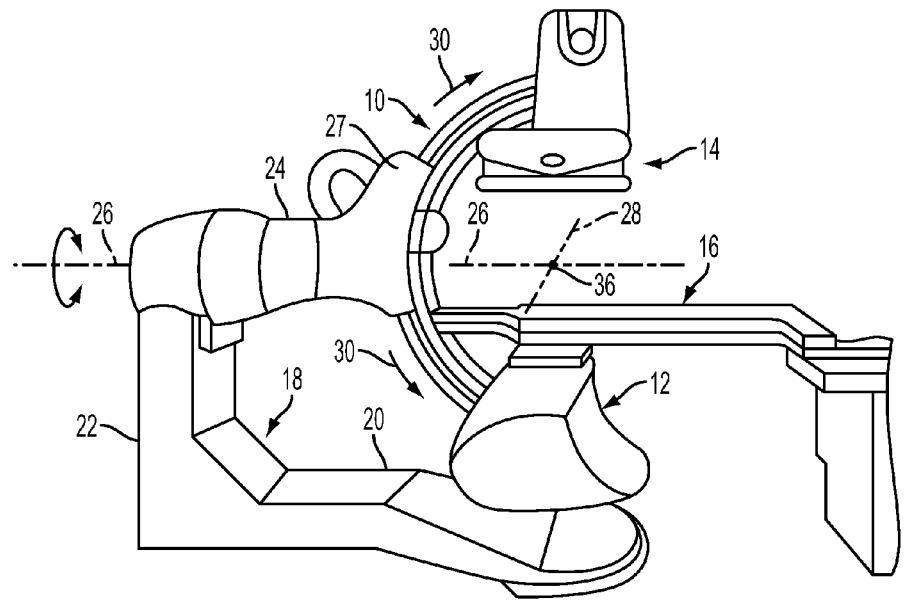
FIGS. 1A and 1B depict a rotational x-ray system configured to carry out a process in accordance with the present invention.
Figure 1B:
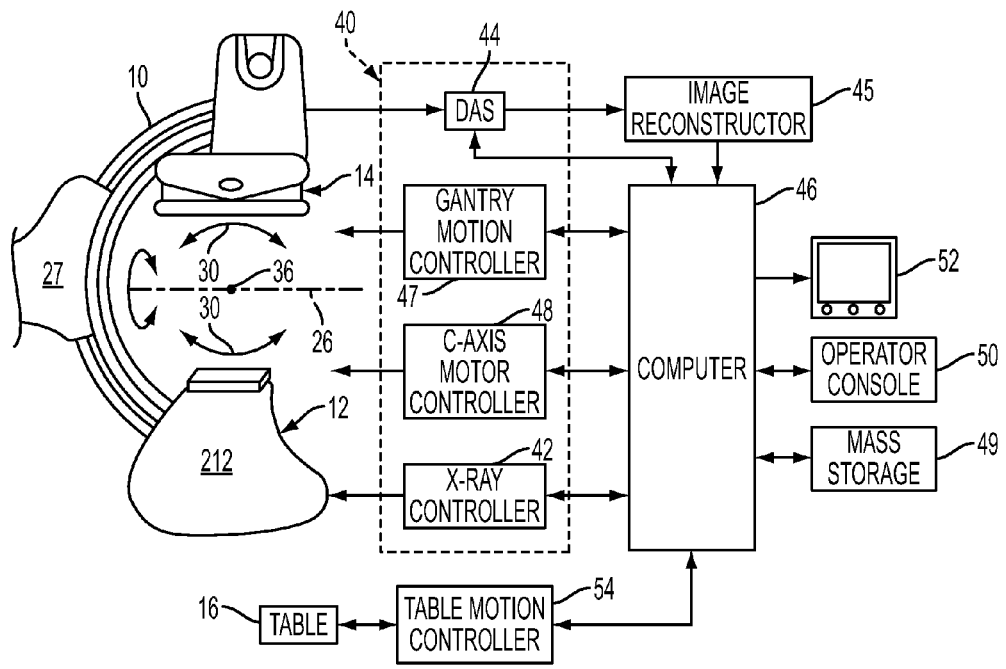

An embodiment a data collection apparatus is a C-arm system such as that shown in FIGS. 1A and 1B. Referring to FIG. 1A, some embodiments may employ a rotational x-ray system that is designed specifically for use in connection with interventional procedures. The system includes a gantry having a C-arm 10 which carries an x-ray source assembly 12 on one of its ends and an x-ray detector array assembly 14 at its other end. The gantry enables the x-ray source 12 and detector 14 to be oriented in different positions and angles around a patient disposed on a table 16, while enabling a physician access to the patient.

The gantry includes an L-shaped pedestal 18 which has a horizontal leg 20 that extends beneath the table 16 and a vertical leg 22 that extends upward at the end of the horizontal leg 20 that is spaced from of the table 16. A support arm 24 is rotatably fastened to the upper end of vertical leg 22 for rotation about a horizontal pivot axis 26. The pivot axis 26 is aligned with the centerline of the table 16 and the arm 24 extends radially outward from the pivot axis 26 to support a C-arm drive assembly 27 on its outer end. The C-arm 10 is slidably fastened to the drive assembly 27 and is coupled to a drive motor (not shown) which slides the C-arm 10 to revolve it about a C-axis 28 as indicated by arrows 30. The pivot axis 26 and C-axis 28 intersect each other at an isocenter 36 located above the table 16 and they are perpendicular to each other.

The x-ray source assembly 12 is mounted to one end of the C-arm 10 and the detector array assembly 14 is mounted to its other end. The x-ray source 12 emits a beam of x-rays which are directed at the detector array 14. Both assemblies 12 and 14 extend radially inward to the pivot axis 26 such that the center ray of this beam passes through the system isocenter 36. The center ray of the beam can thus be rotated about the system isocenter around either the pivot axis 26 or the C-axis 28, or both during the acquisition of x-ray attenuation data from a subject placed on the table 16.

The x-ray source assembly 12 contains an x-ray source which emits a beam of x-rays when energized. The center ray passes through the system isocenter 36 and impinges on a two-dimensional flat panel digital detector housed in the detector assembly 14. The detector is a 2048 by 2048 element two-dimensional array of detector elements having a size of 41 cm by 41 cm. Each element produces an electrical signal that represents the intensity of an impinging x-ray and hence the attenuation of the x-ray as it passes through the patient. During a scan the x-ray source assembly 12 and detector array assembly 14 are rotated about the system isocenter 36 to acquire x-ray attenuation projection data from different angles. The detector array is able to acquire 30 projections, or views, per second and this is the limiting factor that determines how many views can be acquired for a prescribed scan path and speed.

Referring particularly to FIG. 1B, the rotation of the assemblies 12 and 14 and the operation of the x-ray source are governed by a control mechanism 40 of the x-ray system. The control mechanism 40 includes an x-ray controller 42 that provides power and timing signals to the x-ray source 32. A data acquisition system (DAS) 44 in the control mechanism 40 samples data from detector elements 38 and passes the data to an image reconstructor 45. The image reconstructor 45, receives digitized x-ray data from the DAS 44 and performs high speed image reconstruction according to the methods of the present invention. The reconstructed image is applied as an input to a computer 46 which stores the image in a mass storage device 49 or processes the image further to produce parametric images according to the teachings of the present invention. It is contemplated that the computer 46 may be or include components of a digital vascular image processor (DVIP) system.

The control mechanism 40 also includes gantry motor controller 47 and a C-axis motor controller 48. In response to motion commands from the computer 46 the motor controllers 47 and 48 provide power to motors in the x-ray system that produce the rotations about respective pivot axis 26 and C-axis 28. As will be discussed below, a program executed by the computer 46 generates motion commands to the motor drives 47 and 48 to move the assemblies 12 and 14 in a prescribed scan path.

The computer 46 also receives commands and scanning parameters from an operator via console 50 that has a keyboard and other manually operable controls. An associated cathode ray tube display 52 allows the operator to observe the reconstructed image and other data from the computer 46. The operator supplied commands are used by the computer 46 under the direction of stored programs to provide control signals and information to the DAS 44, the x-ray controller 42 and the motor controllers 47 and 48. In addition, computer 46 operates a table motor controller 54 which controls the motorized table 16 to position the patient with respect to the system isocenter 36.

Data are collected during a rotation of the C-arm system. For perfusion measurements mask sweeps are made before the introduction of contrast material. If it is intended to do multiple sweeps using alternating rotation directions, mask projections are obtained with pre-contrast sweeps in each rotational direction.

Figure 2A:
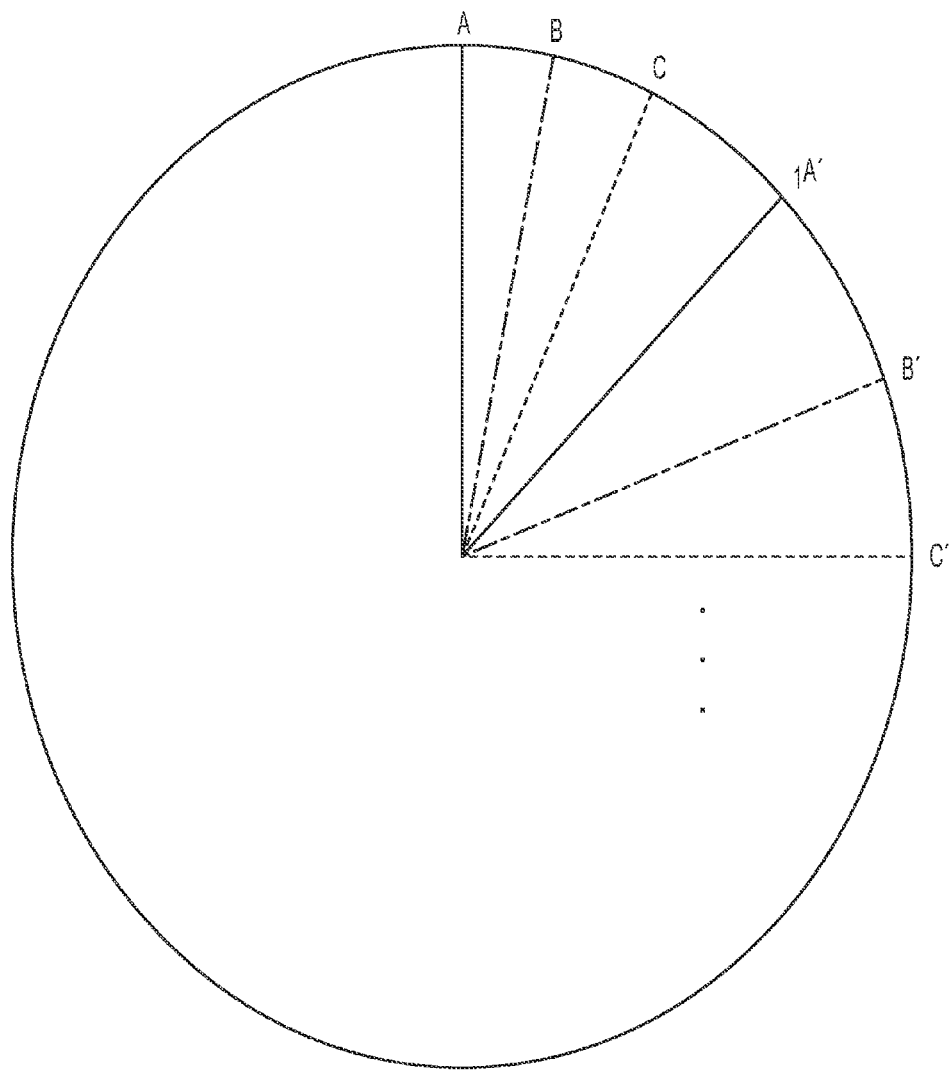
FIGS. 2a and 2B are schematics illustrating the use of limited sectors of X-ray projections to form a time series of 3D volumes.
Figure 2B:
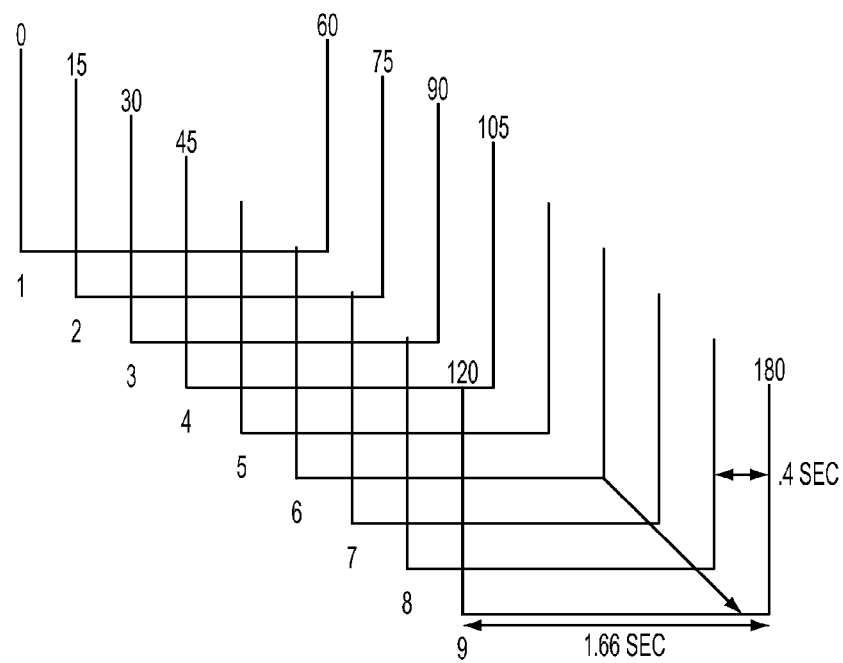

Following the introduction of contrast one or more sweeps are made and the projection data are logarithmically subtracted from the pre-contrast projections to give a series of subtracted projections incrementing in time and angle. In order to maintain temporal resolution the projections are grouped into a series of sectors, e.g., covering a 60 degree angular range (e.g., ranges A-A', B-B', and C-C') and incremented by, e.g., 15 degrees using a sliding window grouping technique shown in FIG. 2A. FIG. 2B shows an entire 180 degree C.-Arm sweep divided in to sectors covering a 60 degree angular range and incremented by 15. As shown, each sector corresponds to a temporal period of 1.66 seconds. Each sector may included one or more projections, e.g., 1, 2, 3, 4, 5, 6, 7, 8, 9, 10 or more projections. In various embodiments, the sectors may range over, e.g., 120 degrees or less, 100 degrees or less, 90 degrees or less, 60 degrees or less, etc. In various embodiments, the ranges may be incremented by, e.g., 45 degrees or less, 30 degrees or less, 15 degrees or less, etc. In various embodiments, the temporal period of the sectors may be 5 seconds or less, 2 seconds or less, 1 second or less, etc. In various embodiments, any other suitable choices for the sector range, increment, projection number, or temporal period may be used.

Figure 3A:
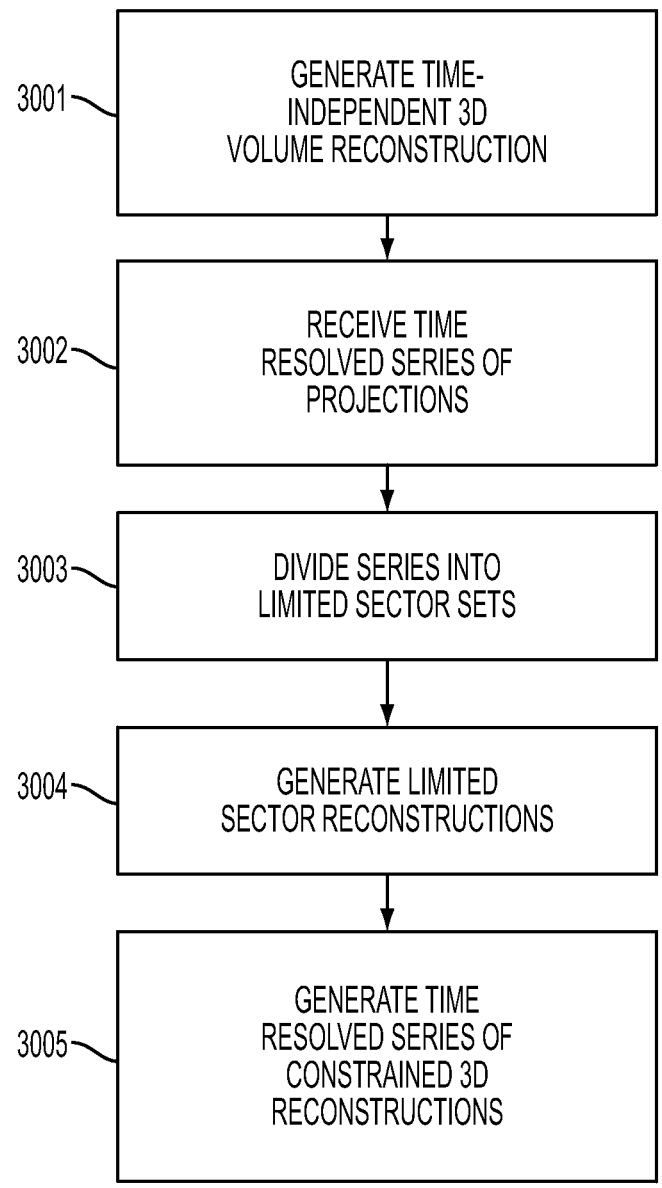
FIG. 3A is a flow chart form an image processing method.

FIG. 3A shows an exemplary method of for generating a time resolved series of 3D reconstructions based on limited sector sets of projections. In step 3001, a time independent 3D volume reconstruction of an area of interest (e.g., containing blood vessels and a surrounding perfusion bed) is generated. The time independent volume may be generated based on a series of projections acquired over a wide range of angles, e.g., about 180 degrees or more. For example, the range may be the full 180 degree range of a C-arm system described above, plus the angle subtended by the corresponding detector.

In step 3002, a time resolved series of projections in received, e.g., from the C-Arm system described above. In step 3003, the series of projections is divided in limited sector sets, e.g., using the sliding window technique described above.

In step 3004, each of the limited sector sets is used to generate a limited sector 3D volume reconstruction, e.g., using filtered back projection, or any other suitable reconstruction technique known in the art.

In step 3005, the limited sector 3D volume reconstructions are constrained by (e.g., via a multiplication with) the time independent 3D volume reconstruction to generate a time resolved series of constrained 3D reconstructions. In some embodiments, the series of constrained reconstructions provides good imaging of the perfusion bed, and are referred to as a 4D perfusion images. In some embodiments, the 4D perfusion images may be further processed, e.g., to produce parametric images as described in detail below.

Figure 3B:
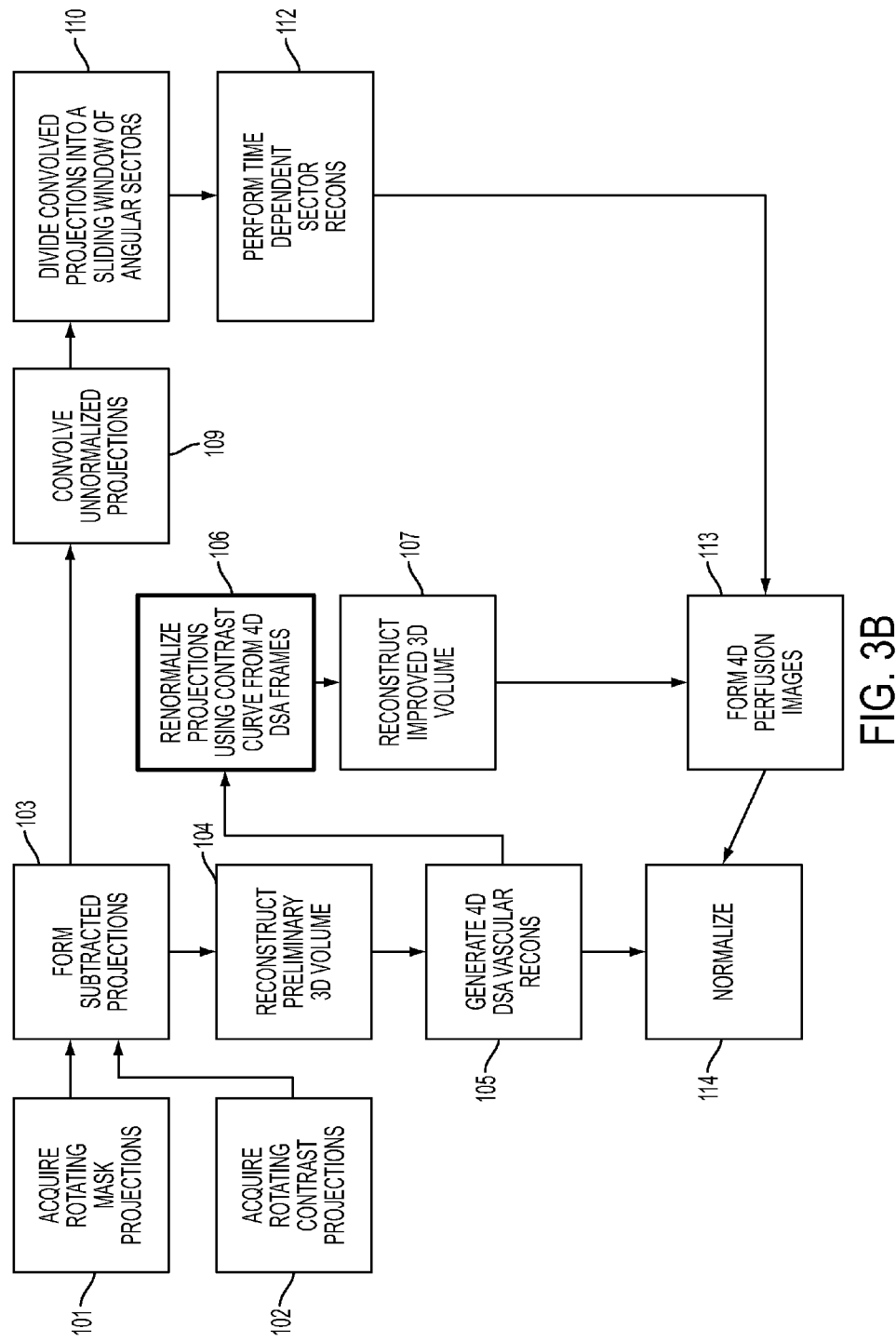
FIG. 3B is a schematic illustrating one possible method for reconstructing a time series of 3D volumes that provide perfusion information.

An exemplary processing sequence is illustrated in FIG. 3B. Mask and contrast projections are obtained in processing blocks 101 and 102 and are logarithmically subtracted in block 103. From these, a preliminary 3D volume reconstruction is performed in block 104 using standard approximate cone-beam CT methods. This volume is used in conjunction with a limited number of projections, typically two per time frame to generate a series of 4D DSA vascular reconstructions in block 105 with good temporal resolution, typically on the order of 5-15 per second as described in a U.S. patent application Ser. No. 12/692,340, incorporated by reference above.

The contrast information from the 4D DS time frames are used to renormalize the projections in block 106 so that a better 3D volume can be constructed in block 107 with more uniformly weighted projections. Since the contrast curves in various portions of the image will be somewhat different, this is an approximate correction for the contrast generated non-uniformities versus time. When the projection set used to construct the 3D volume has vessels missing that have not yet filled, this renormalization can not restore them but can provide a better rendition of vessel that are present in most of the projections. An alternate normalization scheme is presented below in reference to FIG. 4.

It is to be understood that the projections acquired for the time independent 3D DSA reconstruction may differ from those used to form the time dependent 4D DSA perfusion images. In particular the time dependent images should include projections in which contrast is flowing into the system demonstrating changes in perfusion. The data for the time independent, large angular range 3D DSA reconstruction should be obtained in the equilibrium phase. Therefore, in typical embodiments, the projection acquisitions for the time dependent and time independent reconstructions are preferably obtained during different sweeps of the C-arm, In block 109 the unrenormalized projections are convolved and divided into a temporally sliding window of angular sectors in block 110 for use in reconstructing time dependent sector reconstructions in block 112. Note in some embodiments the convolution of block 109 is omitted, and the time dependent limited sector reconstruction formed from unconvolved projections. The sector reconstructions can then be subsequently convolved.

In block 113, the time dependent sector reconstructions are combined (e.g. multiplied with) with the improved 3D volume to produce a serried of constrained, time resolved 4D perfusion images.

In block 114, the 4D perfusion images and 4D DSA vascular reconstructions may be combined to provide normalized images, e.g., which correct for angular variations, as described in detail below.

The use of limited sectors generates blurring. In particular for the frames generated from angles predominantly from the lateral direction, the maximum intensity projection (MIP) images from the lateral direction are sharp. However the MIP images from the anteroposterior (AP) direction are blurry. Similarly, when the sector angles are predominantly from the AP direction, the AP MIP images are sharp and the lateral MIP images are blurry. However, the convolution that is applied to the time frame data generally produces an amount of blurring similar to that of the sector reconstruction. This fact allows for the use of sector data to increase temporal resolution without an unacceptable loss is spatial resolution.

Figure 4:
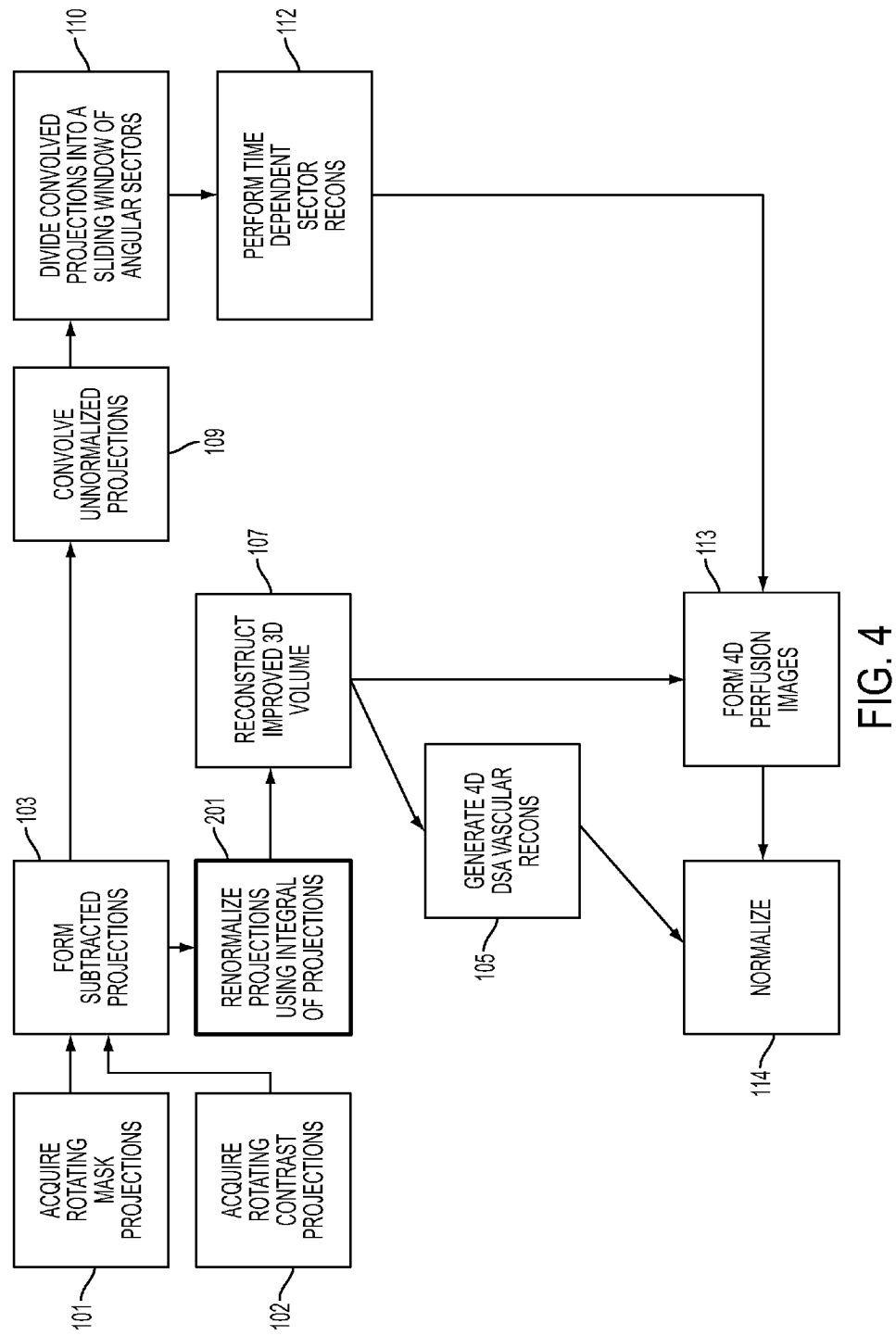
FIG. 4 is a schematic illustrating an alternative method for reconstructing the constraining image and the subsequent perfusion time frames.

In FIG. 4, in block 201 the subtracted projections of block 103 are renormalized using the sum of projected rays at each angle instead of using the 4D DSA information. It is well known that the ray sums should be the same at all angles. This is the Helgason-Ludwig consistency condition and reflects the fact that the net attenuation going through an object entirely within the field of view has to be the same in the absence of ray truncation. Thus the projections may be divided by the sum calculated at the central angle for the time frame in question. This procedure renormalizes any variations in the projection sum due to contrast variations that may occur within the angular sector and also corrects for any variations in X-ray tube output within the sector. Following this option, the processing proceeds as in FIG. 3.

When limited angle sector reconstructions are performed, the reconstructed values in any chosen slice of the imaging volume can depend on the orientation of the sector relative to the plane in question. The variations on the reconstructed values as a function of sector orientation can not, in typical embodiments, be predicted solely on the sector orientation. Instead, they also depend on the distribution of anatomy and the variations this anatomy produces for various sector orientations. There are at least two techniques that can minimize variations in reconstructed values due to the various sector orientations within a given sweep.

In a first technique, the range of sectors within a sweep is chosen to be symmetric about the plane of interest, leading to a reduction of angular variation. For example, in one embodiment, the range of sectors within a sweep is chosen so that the central time frame has a sector that is perpendicular to the plane to be reconstructed. For example, for examination of stroke in a brain it is often desirable to look at an AP plan parallel to the patients face. In this case the central C-arm orientation is vertical oriented, i.e. perpendicular to the selected plane. Accordingly, time frames are calculated using sector orientations symmetrically placed around the vertical position.

A second technique for reducing variations due to sector orientation is to make an explicit angular correction to the temporal values of the 4D perfusion images based on 4D DSA signal values obtained for discrete vessels lying in the selected plane near to any desired region of interest in the perfusion bed in which perfusion is to be calculated. The 4D DSA vessel signal reconstructions are not subject to the limited sector angular variation and provide a model for the shape of the perfusion curve in the surrounding bed, even though there may be some differences due to the difference in the temporal characteristics of the vessels and the adjacent perfusion bed. These differences may be small compared to the sector associated angular variations.

For example, let $V(\theta)$ be the angular variation of the 4D DSA signal as a function of the projection angle $\theta$. Let $P(\theta)$ be the angular variations in the perfusion bed. The reconstructed perfusion signal $PER(\theta)$ may be corrected as PERcorrected($\theta$)=PER($\theta$)*$V(\theta)$/$P(\theta)$ This will impose a first order correction to the perfusion values that should partially remove the variations due to intervening anatomy.

Similarly, one can normalize the perfusion signal vales by comparing the 4D DSA vessel signal and the corresponding signal generated for the same vessel using the sector reconstruction. The ratio of the vessel signals created by both reconstructions can be used to normalize the nearby tissue bed signal in the same slice.

Accordingly, if S(vessel4DDSA) is the vessel signal generated by the 4D DSA reconstruction and S(vessel sector) is the same vessel reconstructed using the perfusion sector reconstruction, then the normalized tissue bed signal S(bed-norm) is given by S(bed-norm)=S(bed-sector)*S(vessel4DDSA)/S(vessel Sector).

The normalization block 114 in the processes shown in FIGS. 3B and 4 may implement any of the above techniques.

Figure 11:
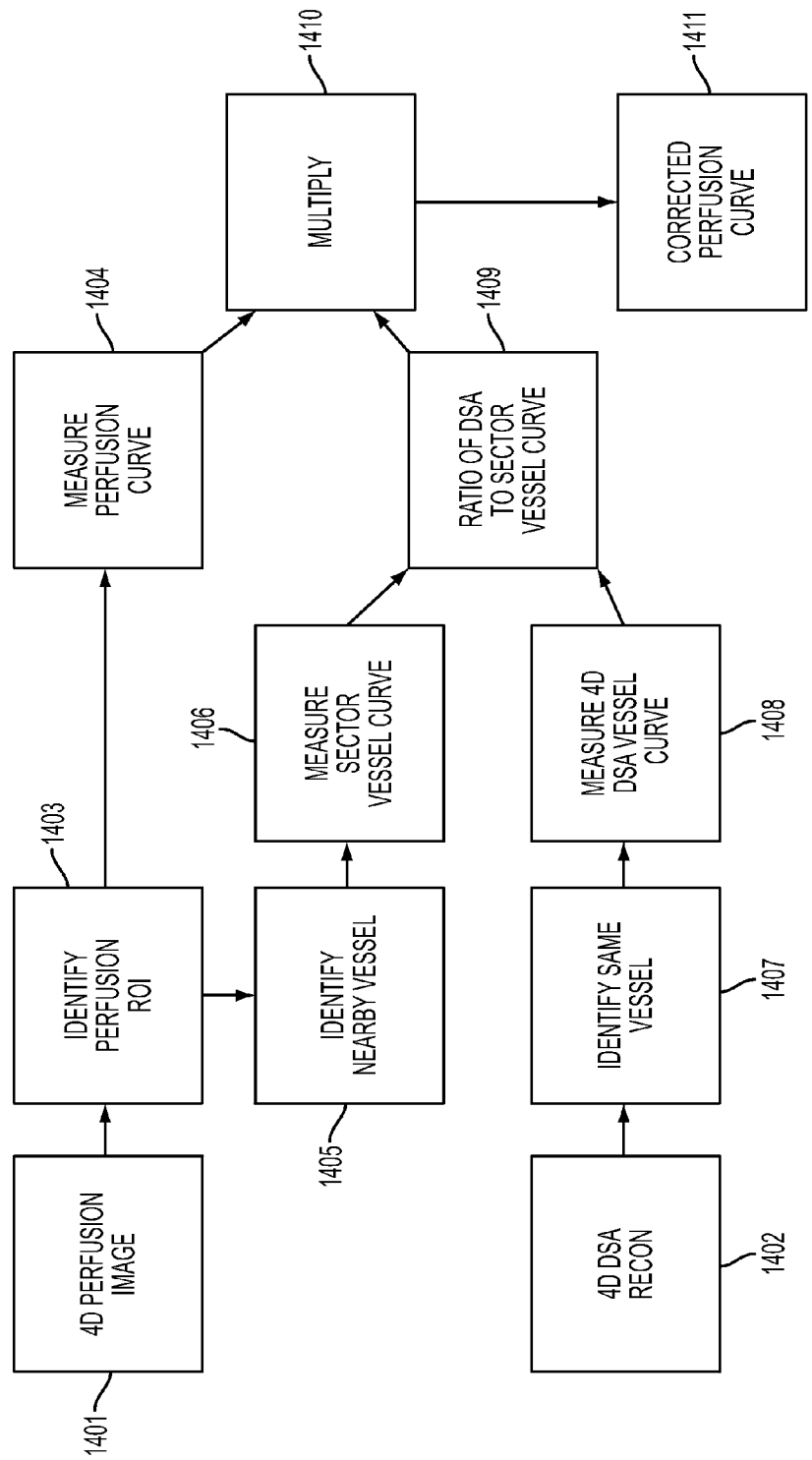
FIG. 11 illustrates an exemplary embodiment of the normalization process block 114 shown in FIGS. 3B and 4.

For example, FIG. 11 shows an exemplary normalization process. In block 1401 4D perfusion images based on sector reconstruction are received. In block 1402 4D DSA vascular reconstructions not based on sector reconstruction are received.

In block 1403 a perfusion region of interest (ROI) is identified, and in block 1404 a perfusion curve is measured for the ROI.

In block 1405 a blood vessel is identified which is in proximity to the perfusion ROI. In block 1406 a sector vessel curve indicative of the time dependence of portion of in the 4D perfusion images corresponding to the vessel. In block 1407 the same blood vessel is identified in the 4D DSA vascular reconstructions. In block 1408, a 4D DSA vessel curve indicative of the time dependence of portion of in the 4D DSA reconstructions corresponding to the vessel.

In block 1409, a ratio is calculated based on the sector and 4D vessel curves. In block 1410, this ratio multiplies the perfusion curve from block 1404 to generate a corrected perfusion curve in block 1411

FIG. 5A illustrates the acquisition of projections during multiple sweeps of the C-arm. FIG. 5A shows pre contrast forward sweeps (block 301) and reverse sweeps (block 302 of the c-arm to obtain mask projections required for cancellation of anatomy.

Following injection the C-arm sweeps are reversed as indicated in blocks 303 through 306. This sweep reversal may be continued throughout the passage of the contrast. The pre contrast sweep data are subtracted from the corresponding post contrast data to form subtraction images as in conventional DSA. As mentioned earlier, the initial sweeps are best suited for acquisition of inflow information. Subsequent sweeps can be used to provide data for the time independent 3D DSA reconstructions.

Figure 5B:
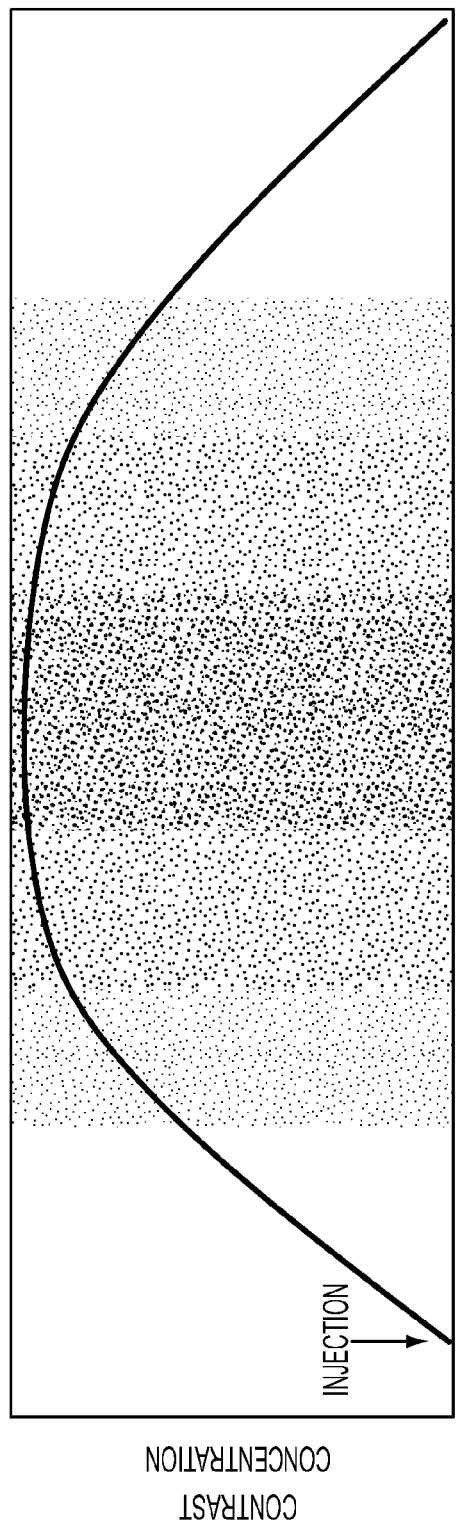
FIG. 5B illustrates contrast level as a function of time after injection.

FIG. 5B illustrates the contrast concentration in the region of interest as a function of time from the injection. After the injection, the contrast washes in to the blood vessels and perfusion bed during an inflow period. The contrast level then reaches a constant value during an equilibrium period. Finally, the contrast washes out during on outflow period. In some embodiments the time independent 3D volume reconstruction is based on projections obtained during the equilibrium period while an inflow set of the time resolved series of image projections used to generate a portion of the 4D perfusion images is obtained during the inflow period; and an outflow set of the time resolved series of image projections used to generate a portion of the 4D perfusion images is obtained during the outflow period.

Figure 12:
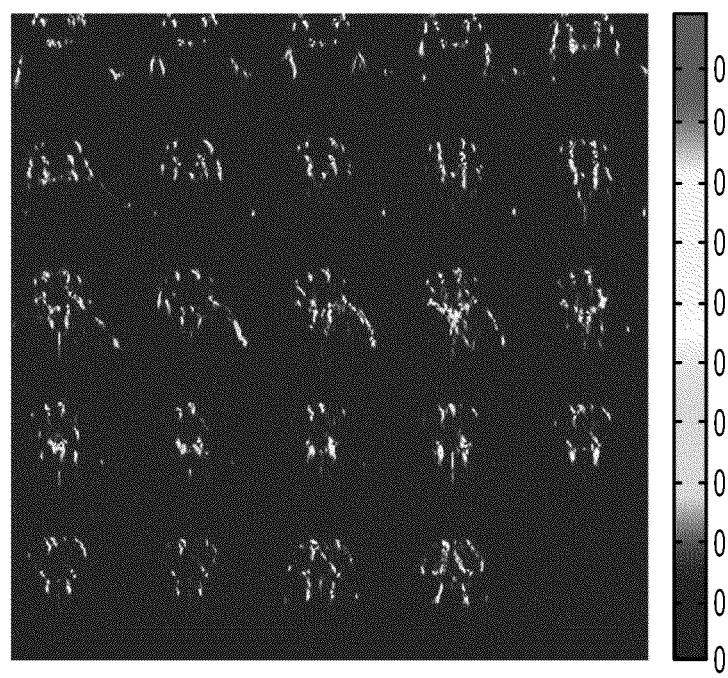
FIG. 12 shows exemplary parametric images generated using the techniques describe herein.
Figure 13:
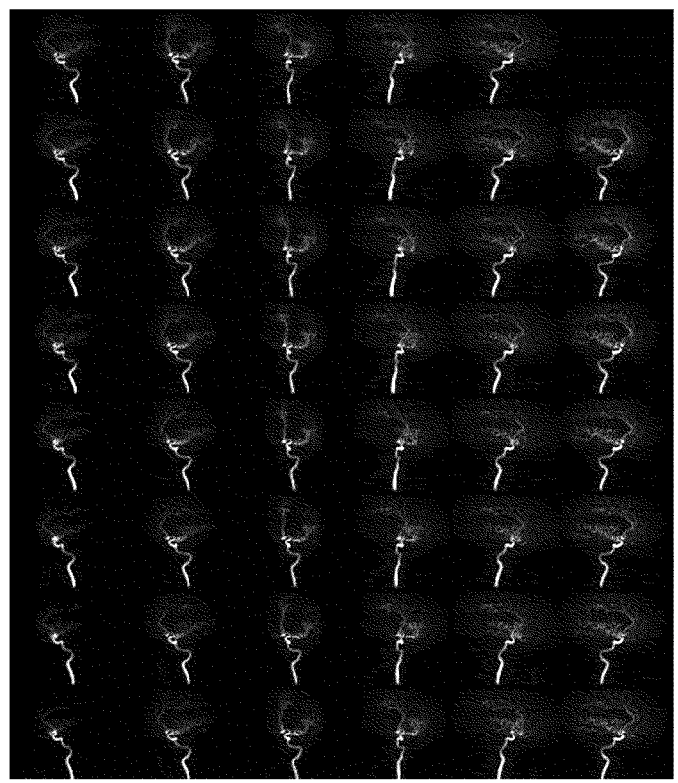
FIG. 13 shows 2D slices of a time resolved series of 4D perfusion images generated using the techniques describe herein.

Parametric images (e.g., as shown in FIG. 12) may be formed from the time dependent information in the individual voxels of the 4D perfusion images. An advantage of the 4D DSA perfusion methods of the type described herein is that the time dependence can be analyzed in individual slices in the image volume without the overlap of slice that occurs in conventional DSA. Techniques described herein permit volume region specific analysis of DSA data. As in conventional DSA parametric images such as mean transit time, time to peak opacification, (TTP), maximum achieved intensity (Cmax), and parameters which characterize flow using a combination of these such as the ratio of Cmax to TTP. These capabilities are available using conventional computed tomography systems where rapid gantry rotations provide sufficient time resolution to provide time dependent volume information. Having this capability in a C-arm X-ray interventional suite allows physicians to evaluate interventions without having to transfer patients to a conventional CT suite.

Figure 6A:
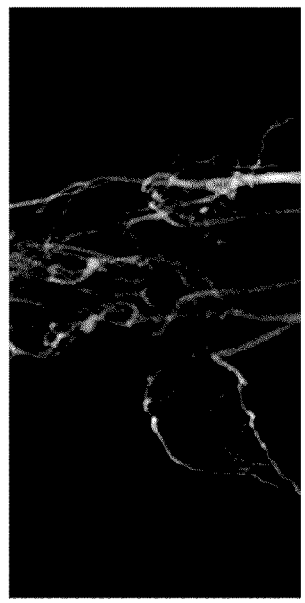
FIGS. 6A and 6B illustrates the use of a grey scale transformation to suppress strong vessel signals that might cast artifacts over the perfusion bed due to the blurring that occurs when a sector reconstruction is used.
Figure 6B:
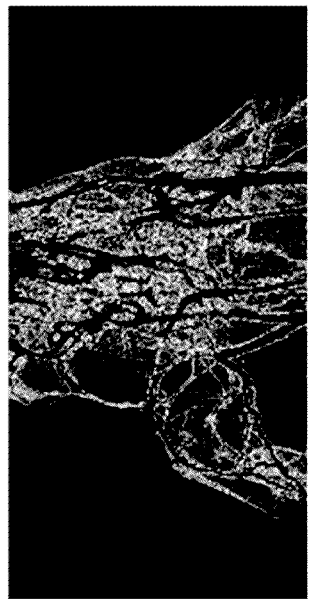

Due to the limited angle reconstruction there can be artifacts that propagate from sources such as vessels to other portions of the volume such as the perfusion bed. Because, in typical applications, practitioners are primarily interested in the perfusion signals, the entire process described above can be done using projections in which the vessels have been suppressed. This can be accomplished by setting to zero all vessel signals above a chosen threshold. This process increases the sensitivity to small perfusion variations. Vessel suppression can be accomplished using a grey scale transformation in which vessel signals in excess of a chosen value are scaled and subtracted from the threshold value. FIGS. 6A-B shows a projection before (A) and after (B) the transformation:

$$\text{projection\_new} = \text{threshold} - \text{projection\_original}/2$$

where threshold refers to the threshold level chosen, projection_new is the grayscale level of the projection shown in FIG. 6A, and projection_original is the grayscale level of the projection shown in FIG. 6B

In addition to the technique of multiplying the sector reconstruction by a constraining image, there are various techniques for improving the quality of the sector reconstruction that provides the low spatial frequency time dependent information. One such technique. is the use of iterative reconstruction. This approach compares projections through the sector reconstruction with the actually acquired projections used to from the sector reconstruction. A fraction of the difference between these two sets of projections can be used to modify the projections used to reconstruct the volume until the projections through the sector reconstructed volume match the acquired projections. To avoid overshoot and oscillation of the solution a fraction of the difference should be used in each iteration. A convergence criterion that specifies how well the original projections and reconstructed projections match can be used to halt the iterative process.

The iterative process can be employed using the basic sector volume reconstruction obtained with limited angle filtered back projection. However, starting with the product of the basic sector reconstruction and the 3D rotational DSA constraining image can accelerate convergence. Both possibilities for the iterative process are illustrated in FIGS. 7a and 7b.

Figure 7A:
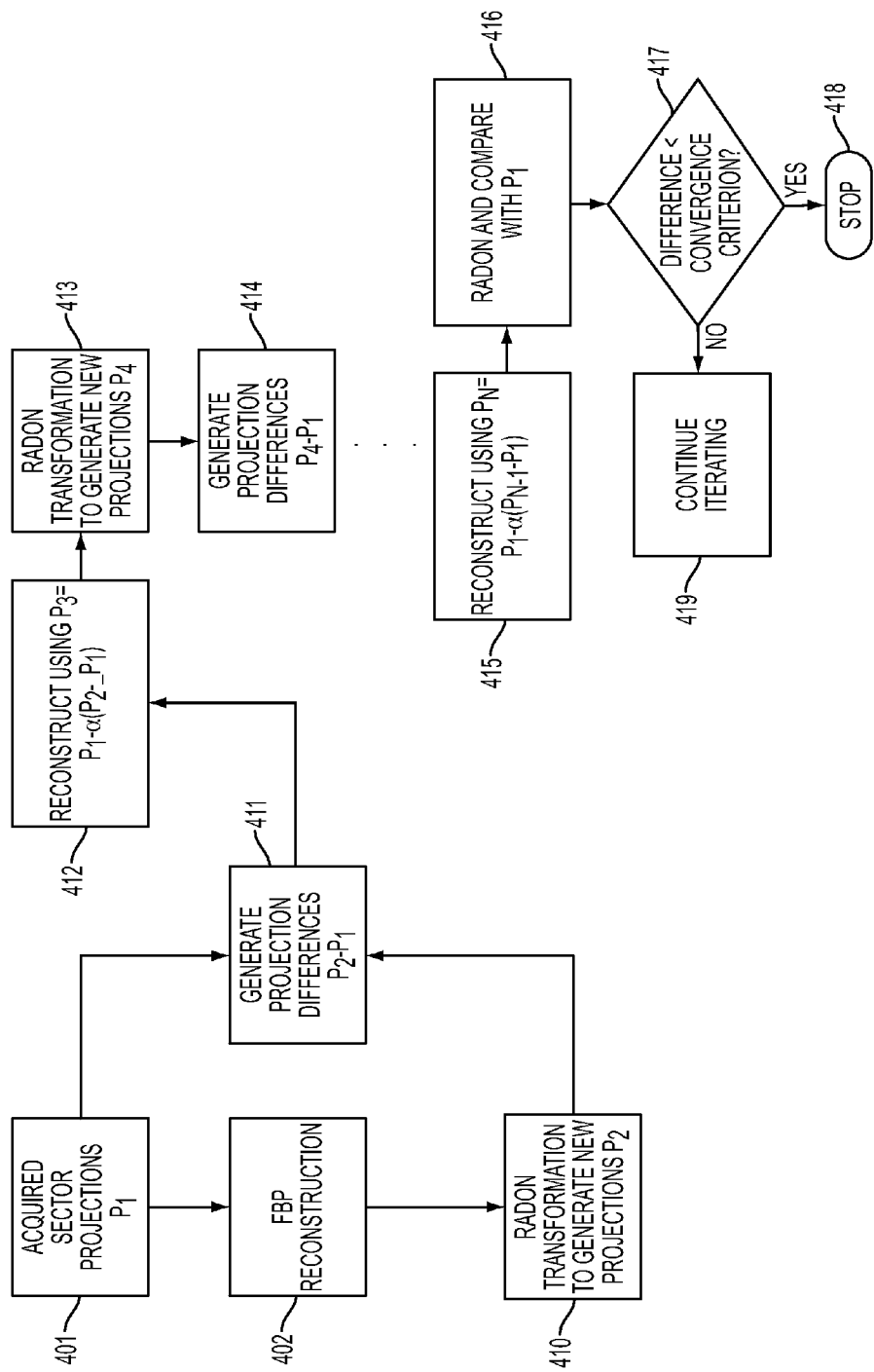
FIGS. 7A and 7B illustrate the steps in an iterative reconstruction procedure designed to improve upon the basic sector reconstruction. The projections regenerated from an iterative series of reconstructions are compared with the originally acquired projections until they are within a chosen convergence criterion.

In FIG. 7A the acquired projections are indicated in processing block 401. These are used to form an initial sector reconstruction using filtered back projection in block 402. Projections from this reconstruction are generated via, e.g., a Radon transformation in block 410 and are used to from projection differences in block 411. At each angle these differences are multiply by a constant a and are subtracted from the original projections and used in block 412 to form the next reconstruction. Projections from this new reconstruction are generated in block 413 and used to form another difference with the originally acquired projections in block 414. This process is continued several times, as indicated by the ellipsis mark. Following blocks 415 and 416 the size of the difference is compared with a convergence criterion in block 417 and the process is stopped in block 418 or continued in block 419.

Artifacts generated by filtered back projection with undersampled projections are spatial frequency dependent. In typical embodiments, for time dependent angiography the projections are uniformly distributed over the surface of the sphere but are very sparse. The positions of the projections are altered for each time frame and are interleaved in position. In order to reduce high spatial frequency artifacts the reconstruction for each time frame is done using more projections at the high spatial frequencies than at the low spatial frequencies. When this is done as a smooth function of spatial frequencies this is called a tornado filter reconstruction. In the case of X-ray projections where sector reconstructions are desired the artifacts due to high spatial frequencies will be worse and there is a potential advantage in using more projection data at high frequencies. The perfusion signal that is desired is predominantly a low spatial frequency signal so that temporal resolution will not be significantly affected if the temporal window for the high spatial frequencies is extended. A scheme for adapting a spatial frequency dependent reconstruction to the X-ray sector reconstruction problem is outlined in FIGS. 7A-7B and 8.

Figure 7B:
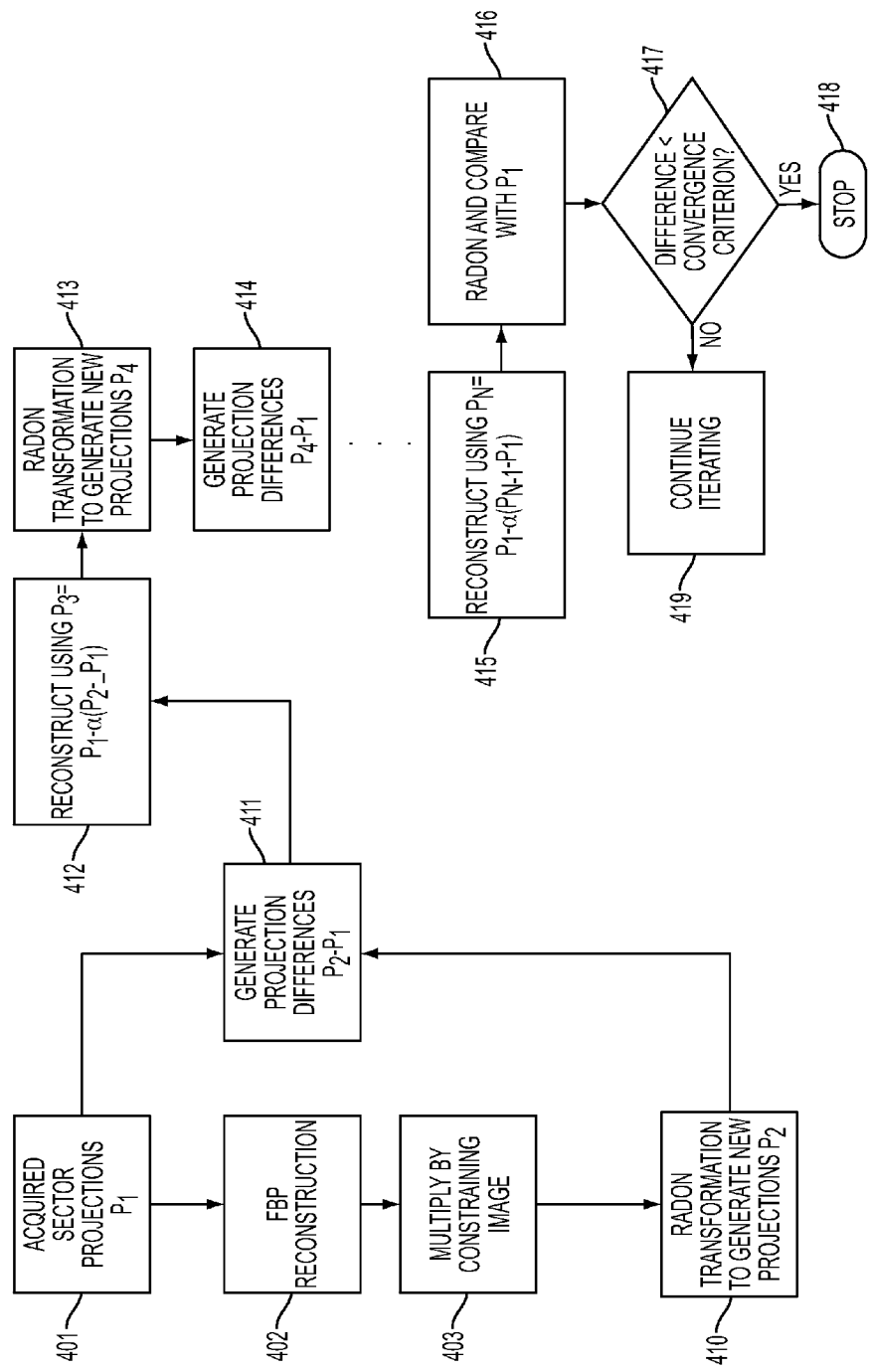

In FIG. 7B, the process described in FIG. 8A is shown for the case in which an additional block 403 in which the FBP reconstruction is multiplied by a constraining image prior to the iterative process shown in FIG. 7A.

Figure 8:
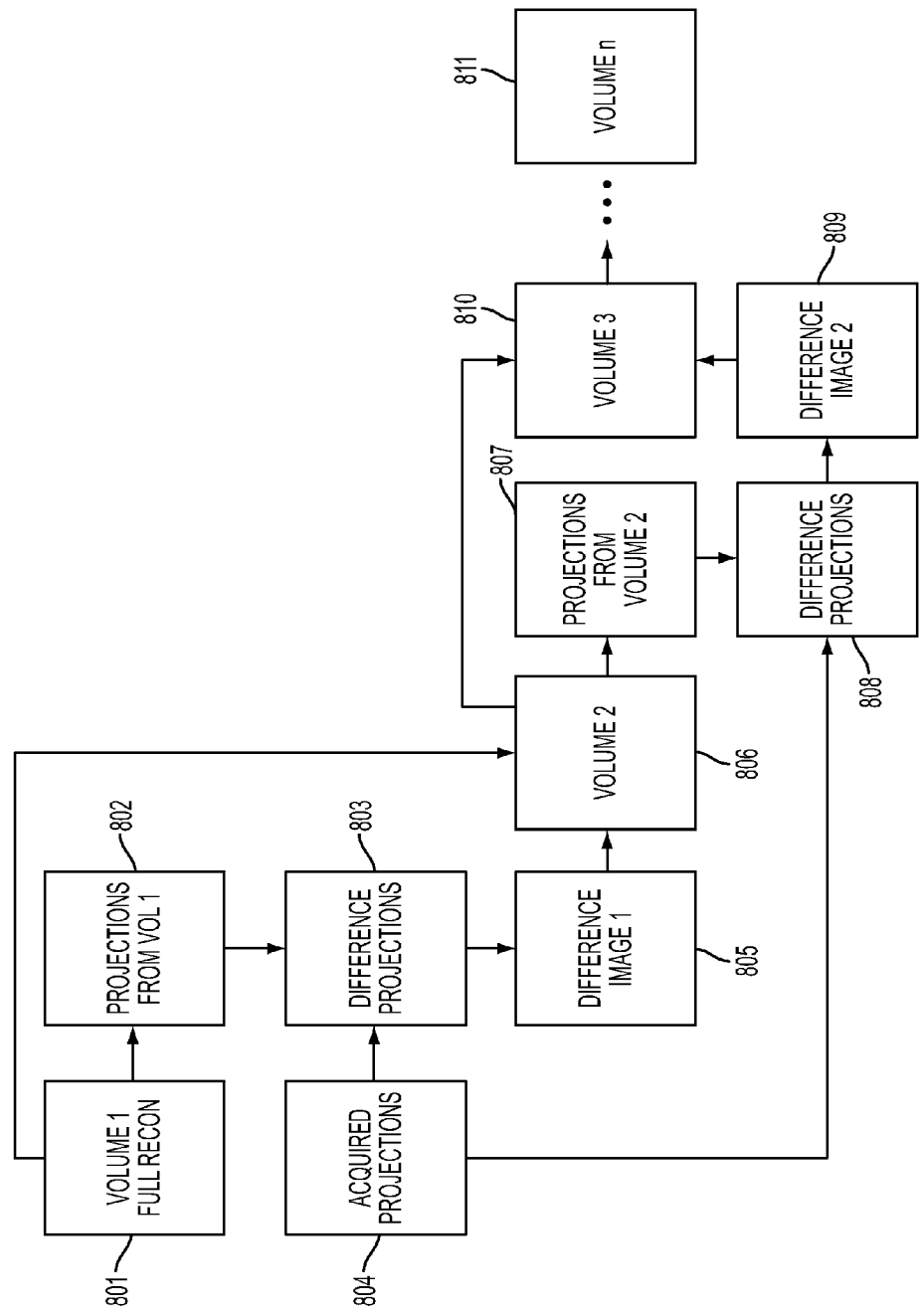
FIG. 8 illustrates an iterative reconstruction in which a series of difference images are used to modify the current image volume estimate

FIG. 8 illustrates an iterative approach in which difference images are generated and used to modify the most recent volume estimate. In block 801 an initial guess at the volume is made. This initial estimate could be the reconstruction using all angles from a given C-arm sweep or it could be an initial limited sector reconstruction or such an image further constrained by a multiplication by an image formed from a wider range of angles. In block 802 the projections from this initial volume, obtained by Radon transformation, are compared with the acquired projections of block 804 in block 803. In block 805 a difference image volume is formed from the difference projections of block 803. In block 806 this difference image is added to volume 1 of block 801 to form volume 2, the most recent estimate. In block 807 projections are formed from volume 2 using, e.g., a Radon transformation and are compared with the acquired projections in block 808. Another difference image is formed from these in 809 and is used to modify volume 2 to form volume 3 in block 810.

As indicated by the ellipsis mark, this process is continued until volume n is generate din block 811 where the process is stopped when the latest set of difference projections are small enough, indicating that the most recent volume produces projections close to the acquired projections.

Figure 9A:
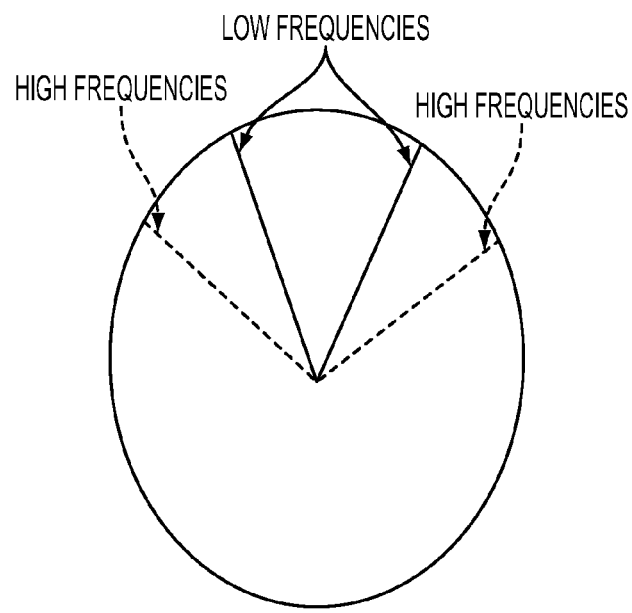
FIGS. 9A and 9B illustrate the choice of separate sector widths at low and high spatial frequencies. For each time frame the low frequency projections span a narrow range, e.g., 60 degrees. The higher frequencies utilize a larger angular range, e.g., 90, 100, 120, 140, 160, 180 or more degrees.
Figure 9B:
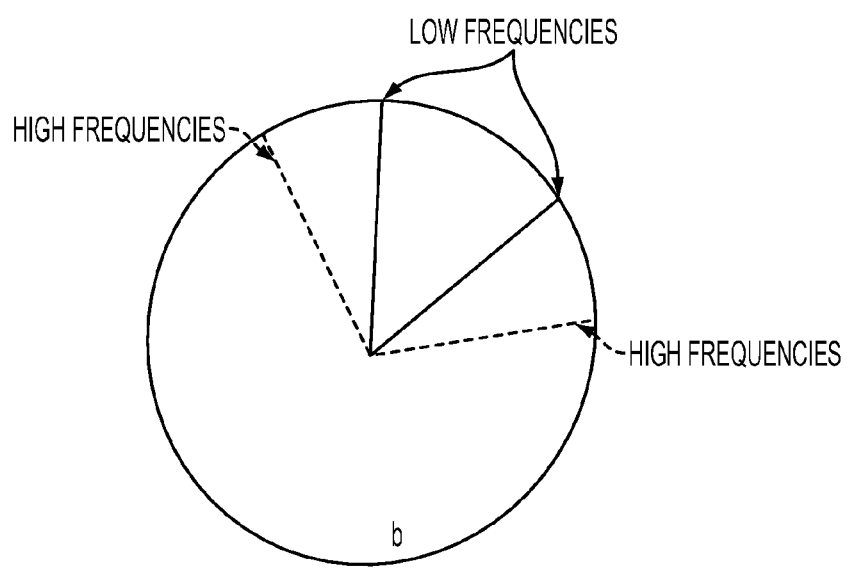

FIGS. 9A-9B illustrate the use of spatial frequency dependent sector lengths. In FIG. 9A a sector corresponding to a first time frame is shown with a narrow projection sector for the low spatial frequencies and a larger sector for the high spatial frequencies. Although only two sectors are shown, in principle this can be done as a continuous function of spatial frequency. FIG. 9B shows a sector corresponding to a later time frame in which both the low and high spatial frequency projection sectors have been rotated.

Figure 10:
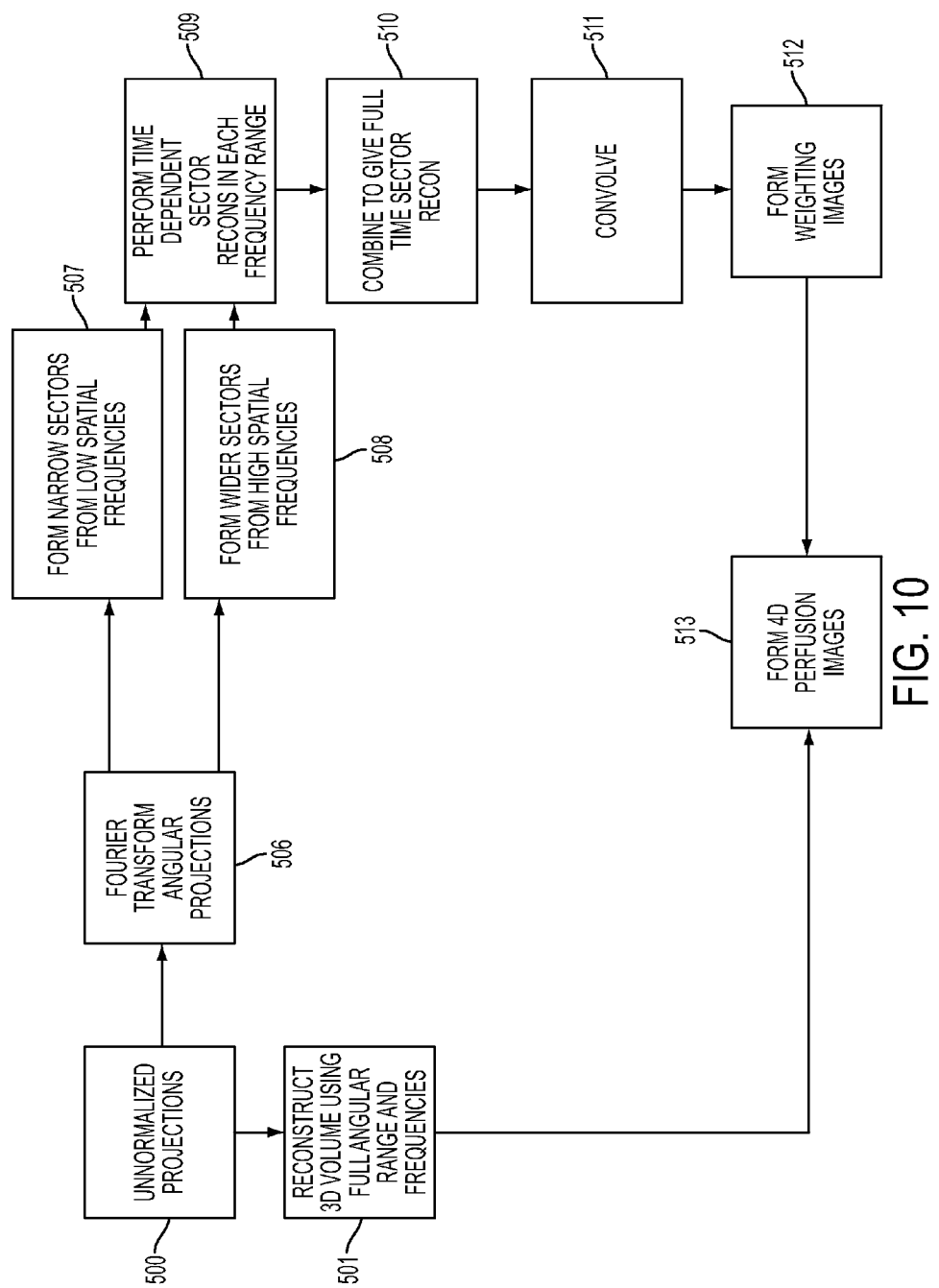
FIG. 10 illustrates the reconstruction scheme using spatial frequency dependent angular sectors.

In FIG. 10 the acquired projections from a C-Arm rotation are shown in processing block 500. From these a reconstruction using the full range of angles and spatial frequencies is performed in block 501. This is eventually used to constrain the reconstruction of the 4D DSA perfusion images in block 513.

In block 506 the time dependent sector projections are Fourier transformed and divided into at least two spatial frequency range in blocks 507 and 508. In block 509 limited sector reconstructions are performed in each frequency range and combined to give a full sector reconstruction in block 510.

In block 511 the reconstructed volumes are convolved and combined with the time independent information of 505 to form weighting images in block 512 that are then combined with the constraining volume of 501 to form 4D perfusion images in block 513.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention.

For example, although in the embodiments described in detail above image projections are received directly from a C-arm system for processing, the images may be received from any other suitable source. For example, the projections may be received (e.g., in real time) from a remote source, e.g., via the internet or outer network. Accordingly, the techniques described herein may be used in telemedical and other such applications. In other embodiments, the projections may be stored, e.g. in database saved on one or more memory devices, and received for processing. Accordingly, the techniques described herein may be used in teaching, simulation, research and other such applications As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

Definitions that are contained in text incorporated by reference are excluded to the extent that they contradict definitions in this disclosure.

For the purposes of this disclosure and unless otherwise specified, "a" or "an" means "one or more."

As used herein, the term "comprising" is intended to mean that the compositions and methods include the recited elements, but not excluding others. "Consisting essentially of" when used to define compositions and methods, shall mean excluding other elements of any essential significance to the combination for that intended purpose. "Consisting of" shall mean excluding more than trace elements of other ingredients and substantial method steps for making or using the concentrators or articles of this invention.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of providing time dependent three dimensional imaging of a region of a patient comprising blood vessels in a perfusion bed, the method comprising:
   generating a time independent 3D volume reconstruction of the region based on a series of image projections of the region acquired over a wide range of projection angles;
   receiving a series of time resolved image projections of the region; and
   generating a time resolved series of limited sector 3D volume reconstructions of the region, wherein generating each limited sector 3D volume reconstruction in the series comprises:
      selecting a respective limited sector set of image projections from the series of time resolved image projections, the limited sector set of image projections including of projections in a limited range of projection angles less than the wide range of projection angles; and
      generating the limited sector 3D volume reconstruction based on the respective limited sector set of projections and constrained by the time independent 3D volume reconstruction.

2. The method of claim 1, wherein the projections are subtracted angiography projections.

3. The method of claim 1, wherein the wide range of angles corresponds to angles spaced over a range of about 180 degrees or more.

4. The method of claim 1, wherein the limited range of angles corresponds to angles spaced over a range of about 100 degrees or less.

5. The method of claim 1, wherein each limited sector set of image projections is selected based on a sliding window applied to the series of time resolved image projections of the region.

6. The method of claim 1, wherein generating each limited sector 3D volume reconstruction based on the respective limited sector set of image projections and constrained by the time independent 3D volume reconstruction comprises:
   generating a limited sector 3D volume reconstruction having relatively low spatial frequency components derived primarily from the respective limited sector set of projections and high frequency components derived primarily from the time independent 3D volume reconstruction.

7. The method of claim 1, wherein generating each limited sector 3D volume reconstruction based on the respective limited sector set of image projections and constrained by the time independent 3D volume reconstruction comprises:
   generating a limited sector 3D volume reconstruction based on the image projections; and
   convolving the limited sector 3D volume reconstruction; and
   multiplying the convolved limited sector 3D volume reconstruction with the time independent 3D volume reconstruction to generate a respective limited sector 3D volume reconstruction constrained by the time independent 3D volume reconstruction.

8. The method of claim 1, wherein generating each limited sector 3D volume reconstruction based on the respective limited sector set of image projections and constrained by the time independent 3D volume reconstruction comprises:
   convolving the image projections in the limited sector set of projections;
   generating a limited sector 3D volume reconstruction based on the convolved image projections; and
   multiplying the limited sector 3D volume with the time independent 3D volume reconstruction to generate a respective limited sector 3D volume reconstruction constrained by the time independent 3D volume reconstruction.

9. The method of claim 1, wherein, during an imaging period:
   a contrast fluid flows into or out of the blood vessels in the region of the patient during a flow period;
   the contrast fluid flow reaches an equilibrium state in the blood vessels in the region during an equilibrium period; and
   wherein:
   the time independent 3D volume reconstruction is based on projections obtained during the equilibrium period; and
   the time resolved series of image projections is obtained during the flow period.

10. The method of claim 1, wherein, during an imaging period:
    a contrast fluid flows into the blood vessels in the region of the patient during an inflow period;
    the contrast fluid flow reaches an equilibrium state in the blood vessels the region during an equilibrium period;
    the contrast fluid flows out of the blood vessels in the region during an outflow period;
    and
    wherein:
    the time independent 3D volume reconstruction is based on projections obtained during the equilibrium period;
    an inflow set of the time resolved series of image projections is obtained during the inflow period; and
    an outflow set of the time resolved series of image projections is obtained during the outflow period.

11. The method of claim 1, further comprising, for at least one limited sector set of projections:
    a) generating a calculated 3D volume reconstruction based on the projections in the limited sector set of image projections;
    b) generating a set of calculated projections based on the calculated 3D volume reconstructions;
    c) comparing the set of calculated projections to the projections in the limited sector set of image projections;
    d) modifying the limited sector set of projections of the based on the comparison;
    e) generating a modified calculated 3D volume reconstruction based on the modified projections;
    f) generating a set of modified calculated projections based on the modified calculated 3D volume reconstruction;
    g) comparing the set of modified calculated projections to the modified projections used to generate the modified calculated 3D volume reconstruction; and
    h) further modifying the modified projections of the based on the comparison.

12. The method of claim 11, further comprising: iteratively repeating steps e-h to improve the similarity of the modified calculated projections to the projections used to generate the limited sector 3D volume reconstruction.

13. The method of claim 11, wherein at least one limited sector 3D volume reconstruction is based on the modified projections.

14. The method of claim 11, wherein generating calculated projections based on the limited sector 3D volume reconstructions comprises applying a Radon transformation to the limited sector 3D volume reconstructions.

15. The method of claim 11, at least one of the calculated 3D volume reconstruction and the modified calculated 3D volume reconstructions is constrained by the time independent 3D volume reconstruction.

16. The method of claim 12, wherein the calculated 3D volume reconstruction and the modified calculated 3D volume reconstruction are not constrained by the time independent 3D volume reconstruction.

17. The method of claim 1, further comprising, for at least one 3D volume reconstruction:
   a) generating a set of calculated projections based on the 3D volume reconstruction;
   b) generating a difference projection based on a difference between the set of calculated projections and the acquired projections on which the 3D volume reconstruction is based;
   c) generating a difference 3D volume reconstruction based on the difference projections; and
   d) creating a modified 3D volume by adding the difference 3D volume to the 3D volume reconstruction.

18. The method of claim 1, wherein generating at least one limited sector 3D volume reconstruction comprises based on the respective limited sector set of image projections includes:
   generating a low spatial frequency 3D volume reconstruction based on the low spatial frequency components of projections in a first subrange of the limited angular range;
   generating a high spatial frequency 3D volume reconstruction based on the high spatial frequency components of projection in a second subrange of the limited angular range smaller than the first; and
   generating the limited sector 3D volume reconstruction based on the low spatial frequency 3D volume reconstruction and the high spatial frequency 3D volume reconstruction.

19. The method of claim 1, further comprising:
   generating an initial series of time resolved 3D volume reconstructions each based on a limited number of projections constrained by the time independent 3D volume reconstruction;
   renormalizing the series of image projections of the region acquired over a wide range of projection angles of time independent projections based on the initial series; and
   generating an improved time independent 3D volume based on the renormalized series.

20. The method of claim 1, further comprising:
   compensating for angular variations in the time resolved series of 3D volume reconstructions based on variations related to the anatomy in the region.

21. The method of claim 20, wherein compensating for angular variations in the time resolved series of 3D volume reconstructions based on variations related to the anatomy in the region comprises:
   observing a time dependence of a given region in the perfusion bed in the time resolved series of 3D volume reconstructions;
   observing a time dependence of a nearby blood vessel in the time resolved series of 3D volume reconstructions;
   measuring the time dependence of a corresponding blood vessel in a time resolved vascular reconstruction that is not subject the angular intensity variations; and
   correcting voxels corresponding to the perfusion bed in the time resolved series of 3D volume reconstructions based on the time dependence of the blood vessel in the time resolved series of 3D volume reconstructions and the time dependence of the corresponding blood vessel in a time resolved vascular reconstruction.

22. The method of claim 21, wherein the blood vessel information comprises reconstruction information which is not substantially subject to the angular variations.

23. A system comprising:
   a C-arm X-ray system;
   a processor configured to receive projection information from the X-ray system and implement the method of claim 1 based on the projection information.

* * * * *